United States Patent [19]

Muraki et al.

[11] Patent Number: 5,286,702
[45] Date of Patent: Feb. 15, 1994

[54] PHTHALIDE COMPOUND AND RECORDING MATERIAL USING THE COMPOUND

[75] Inventors: Yutaka Muraki, Uji; Hidekazu Ishida, Nara; Hajime Kawai, Tsuzuki; Katsuhiko Tsunemitsu, Uji, all of Japan

[73] Assignee: Yamada Chemical Co., Ltd., Kyoto, Japan

[21] Appl. No.: 873,938

[22] Filed: Apr. 24, 1992

[30] Foreign Application Priority Data

Apr. 26, 1991 [JP] Japan ............................ 3-191351

[51] Int. Cl.$^5$ .................. B41M 5/145; B41M 5/30; C07D 307/79
[52] U.S. Cl. .................. 503/220; 549/304; 546/187; 546/196; 548/518; 548/525
[58] Field of Search .......... 549/304; 503/220, 213; 513/213; 546/187, 196; 548/518, 525

[56] References Cited

U.S. PATENT DOCUMENTS

| | | | |
|---|---|---|---|
| 4,808,567 | 2/1989 | Kawai et al. | 503/220 |
| 4,814,320 | 3/1989 | Kawai et al. | 503/220 |
| 4,835,291 | 5/1989 | Kawai et al. | 549/304 |

FOREIGN PATENT DOCUMENTS

| | | |
|---|---|---|
| 0062544 | 4/1984 | European Pat. Off. |
| 0127203 | 12/1984 | European Pat. Off. |
| 2211508A | 7/1989 | United Kingdom |

OTHER PUBLICATIONS

Japanese Patent Publication No. 58-5940 Feb. 1983.
Japanese Application Laid-Open (Kokai) 59-199757 Nov. 1984.
Japanese Application Laid-Open (Kokai) 62-243653 Oct. 1987.
Japanese Application Laid-Open (Kokai) 2-138368 (May 1990).

*Primary Examiner*—C. Warren Ivy
*Assistant Examiner*—A. A. Owens
*Attorney, Agent, or Firm*—David G. Conlin; George W. Neuner

[57] ABSTRACT

The present invention provides a novel phthalide compound represented by the following formula, which rapidly forms blue-blue black color with a developer when it is used as a recording material and, since a color image formed therewith has an intense absorption at 700~50 nm, it is usable for optical character reader;

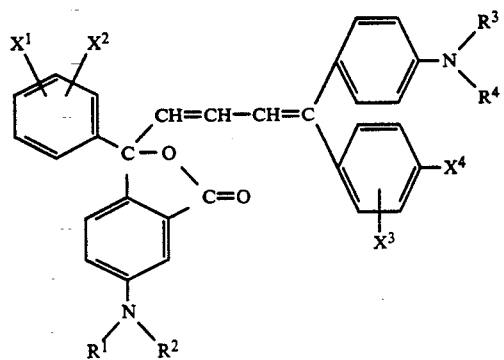

where $R^1$ and $R^2$ represent, independently, alkyl group having 6 or less carbon atoms; cycloalkyl group having 5 or 6 carbon atoms; aryl group; or heterocyclic ring connecting $R^1$, $R^2$ and N, $R^3$ and $R^4$ represent, independently, alkyl group having 6 or less carbon atoms; cycloalkyl group having 5 or 6 carbon atoms; aryl group; a heterocyclic ring connecting $R^3$, $R^4$ and N, $X^1$~$X^3$ represent, independently, hydrogen atom, alkyl group having 6 or less carbon atoms, alkoxy group having 6 or less carbon atom or halogen atom, $X^4$ represents hydrogen atom, alkyl group having 6 or less carbon atoms, alkoxy group having 6 or less carbon atom, halogen atom or 3 Claims, 2 Drawing Sheets

PHTHALIDE COMPOUND AND RECORDING MATERIAL USING THE COMPOUND

BACKGROUND OF THE INVENTION

The present invention relates to a phthalide compound represented by the formula (I):

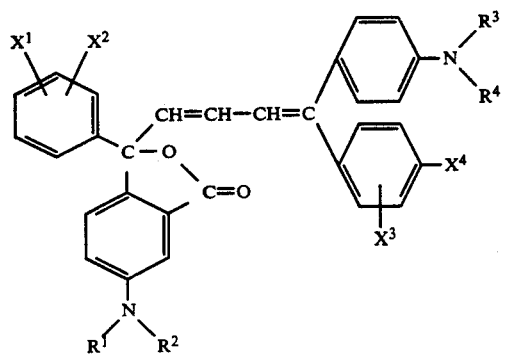

where $R^1$ and $R^2$ represent, independently, alkyl group having 6 or less carbon atoms; cycloalkyl group having 5 or 6 carbon atoms; aryl group; or heterocyclic ring connecting $R^1$, $R^2$ and N, $R^3$ and $R^4$ represent, independently, alkyl group having 6 or less carbon atoms; cycloalkyl group having 5 or 6 carbon atoms; aryl group; or heterocyclic ring connecting $R^3$, $R^4$ and N, $X^1 \sim X^3$ represent, independently, hydrogen atom, alkyl group having 6 or less carbon atoms, alkoxy group having 6 or less carbon atom or halogen atom, $X^4$ represents hydrogen atom, alkyl group having 6 or less carbon atoms, alkoxy group having 6 or less carbon atom, halogen atom or

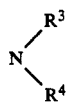

and a recording material using the phthalide compound.

Heretofore, since color images of a blue color forming phthalide compound (compound of the following formula (II)) or a black color forming fluoran compound (compound of the following formula (III)) used as color coupler for recording material has no absorption in a near infrared region, they can not be read by optical character reader:

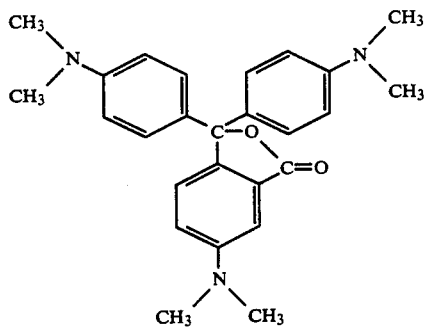

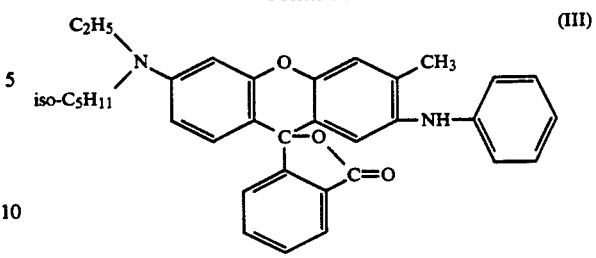

Accordingly, as a color coupler having absorption in the near infrared region, there have been proposed various compounds in each of Japanese Patent Publication Sho 58-5940 (1983), Japanese Patent Laid-Open Sho 59-199757 (1984), 62-243653 (1987) and Japanese Patent Laid-Open Hei 2-138368 (1990).

However, they involve drawbacks in one of color of the compound itself, natural coloring (discoloration of the background), color forming density, light fastness of the background and light fastness of the image. In addition, many of them are difficult to be prepared and no satisfactory color coupler for infrared reading and recording material has yet been provided at present.

That is, the compound described in Japanese Patent Publication Sho 58-5940 (1983) (compound of the formula (IV)) is strongly colored yellow in the compound itself and shows intense natural coloring (discoloration of the background).

The compound described in the Japanese Patent Laid-Open Hei 2-138368 (1990) (compound of the formula (V)) also exhibits intense natural coloring (discoloration of the background). The compound described in Japanese Patent Laid-Open Sho 59- 199757 (1984) (Compound of the formula (VI)) is colorless but not good in the color forming property, absorbance in the near infrared region and the stability of the color image.

Further, the compound described in Japanese Patent Laid-Open Sho 62-243653 (1987) (compound of the formula (VII)) is colored yellow and also insufficient in the light fastness of the images.

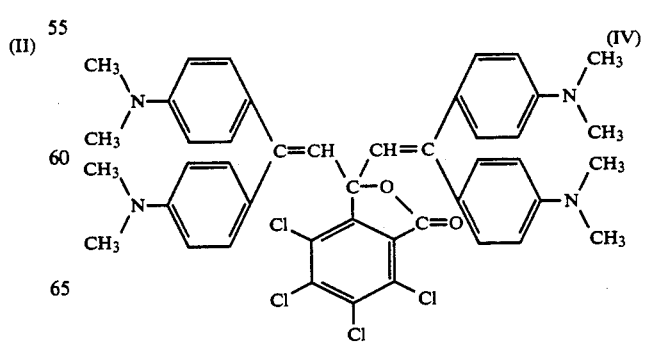

-continued

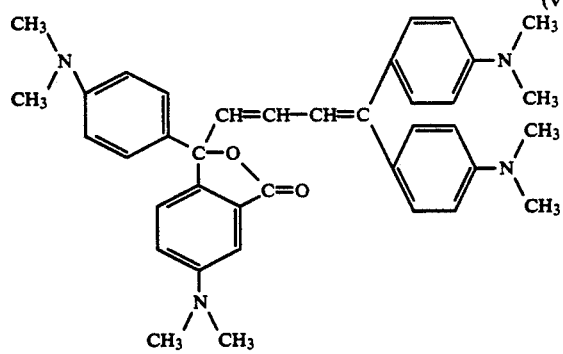

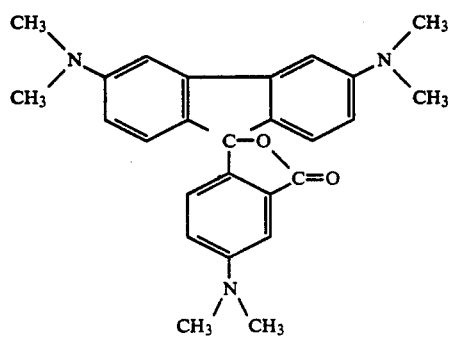

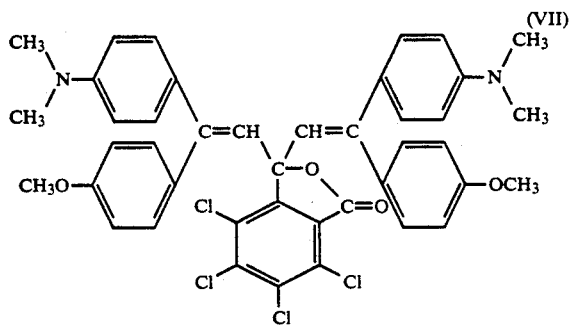

The technical subject of the present invention is to overcome the foregoing drawbacks and provide a compound suitable as a color coupler for infrared reading and recording material.

In the present invention, it has been found that the phthalide compound of the general formula (I) described above is, unexpectedly has excellent properties such as solubility, coloration of the compound itself, hue of formed color, color forming property, absorbance in the near infrared region and image stability.

SUMMARY OF THE INVENTION

An object of the present invention is to provide a phthalide compound represented by the general formula (I) which is a novel compound:

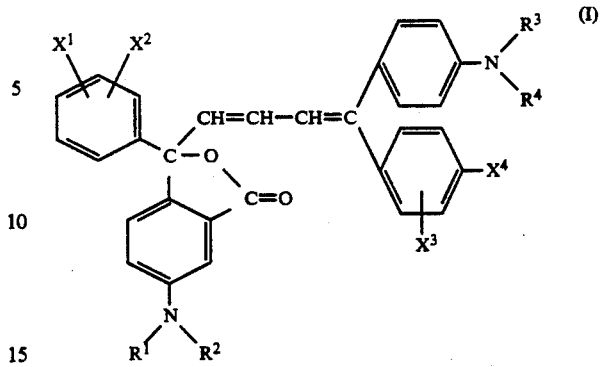

where $R^1$ and $R^2$ represent, independently, alkyl group having 6 or less carbon atoms: cycloalkyl group having 5 or 6 carbon atoms; aryl group such as phenyl group; or heterocyclic ring connecting $R^1$, $R^2$ and N, $R^3$ and $R^4$ represent, independently, alkyl group having 6 or less carbon atoms; cycloalkyl group having 5 or 6 carbon atoms; aryl group or heterocyclic ring connecting $R^1$, $R^2$ and N, $X^1 \sim X^3$ represent, independently, hydrogen atom, alkyl group having 6 or less carbon atoms, alkoxy group having 6 or less carbon atom or halogen atom, $X^4$ represents hydrogen atom, alkyl group having 6 or less carbon atoms alkoxy group having 6 or less carbon atom,
halogen atom or

As the form of the heterocyclic ring connecting $R^1$, $R^2$ and N or $R^3$, $R^4$ and N, there can be mentioned a form of pyrrolidino group, piperidino group etc.

Another object of the present invention is to provide a recording material, for example, pressure sensitive copying paper or heat sensitive recording paper containing the compound of the formula (I) as a color coupler.

DETAILED DESCRIPTION OF THE INVENTION

Figure 1:
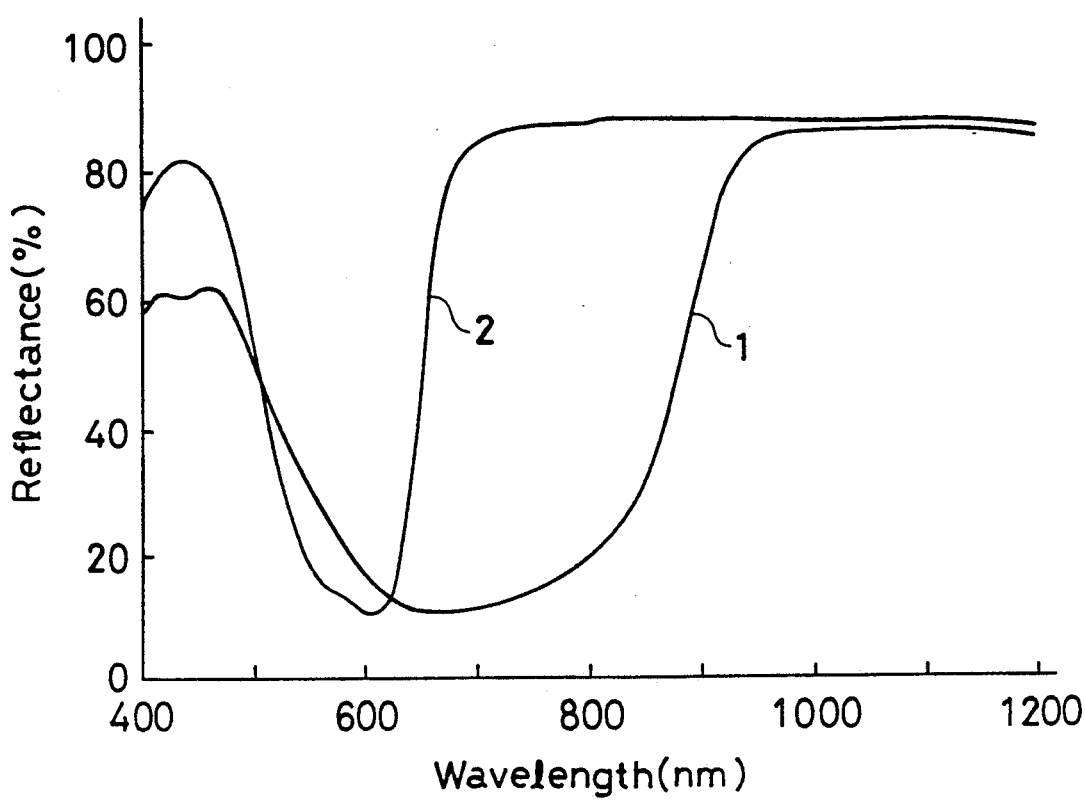
FIG. 1 shows reflection spectra of images in Example 1 and Comparative Example 1.

As concrete examples of the phthalide compound represented by the formula (I), the followings are shown. Each of them is a light color solid, rapidly forming a blue - blue green color with activated clay and has absorption in a near infrared region.

3-phenyl-3-(1,1-bis(4-dimethylaminophenyl)-1,3-butadienyl)-6-dimethylaminophthalide, 3-phenyl-3-(1,1-bis(4-diethylaminophenyl)-1,3-butadienyl)-6-dimethylaminophthalide, 3-phenyl-3-(1,1-bis(4-dimethylaminophenyl)-1,3-butadienyl)-6-diethylaminophthalide, 3-(4-methoxyphenyl)-3-(1,1-bis(4-dimethylamino-
   phenyl)-1,3-butadienyl)-6-dimethylaminophthalide,
3-(4-methoxyphenyl)-3-(1-(4-dimethylaminophenyl)-1-
   (4-diethylaminophenyl)-1,3-butadienyl)-6-dime-
   thylaminophthalide,
3-(4-methoxyphenyl)-3-(1,1-bis(4-diethylaminophenyl)-
   1,3-butadienyl)-6 dimethylaminophthalide,
3-(4-methoxyphenyl)-3-(1,1-bis(4-diethylaminophenyl)-
   1,3-butadienyl)-6-dimethylaminophthalide,
3-(4-methoxyphenyl)-3-(1,1-bis(4-methylbutylamino-
   phenyl)-1,3-butadienyl)-6-dimethylaminophthalide,
3-(2,4-dimethoxyphenyl)-3-(1,1-bis(4-dimethylamino-
   phenyl)-1,3-butadienyl)-6-dimethylaminophthalide,
3-(3,4-dimethoxyphenyl)-3-(1,1-bis(4-dimethylamino-
   phenyl)-1,3-butadienyl)-6-dimethylaminophthalide,
3-(4-ethoxyphenyl)-3-(1,1-bis(4-dimethylaminophenyl)-
   1,3-butadienyl)-6-dimethylaminophthalide,
3-(4-propoxyphenyl)-3-(1,1-bis(4-dimethylamino-
   phenyl)-1,3-butadienyl)-6 dimethylaminophthalide,
3-(4-benzyloxyphenyl)-3-(1,1-bis(4-dimethylamino-
   phenyl)-1,3-butadienyl)-6-dimethylaminophthalide
3-(4-chlorophenyl)-3-(1,1-bis(4-dimethylaminophenyl)-
   1,3-butadienyl)-6-dimethylaminophthalide,
3-(4-methoxyphenyl)-3-(1,1-bis(4-pyrrolidinophenyl)-
   1,3-butadienyl)-6-dimethylaminophthalide,
3-(4-methoxyphenyl)-3-(1,1-bis(4-dimethylamino-
   phenyl)-1,3-butadienyl)-6-pyrrolidinophthalide, 3-(4-
   methoxyphenyl)-3-(1-(4-dimethylaminophenyl)-1-(4-
   methoxyphenyl)-1,3-butadienyl)-6-dimethylaminoph-
   thalide,
3-(4-methoxyphenyl)-3-(1-(4-methylcyclohexylamino-
   phenyl)-1-(4-methoxyphenyl)-1,3-butadienyl)-6-
   methylbutylphthalide,
3-(2,4-dimethoxyphenyl)-3-(1-(4-methylphenylamino-
   phenyl)-1-(3,4-dimethoxyphenyl)-1,3-butadienyl)-6-
   methylbenzylaminophthalide.

The phthalide compound represented by the formula (I) in the present invention can be synthesized by the following procedures.

At first butadiene derivative (compound of the formula (IX)) is synthesized from a ketone (compound of the formula (VIII)) through a Grignard reaction:

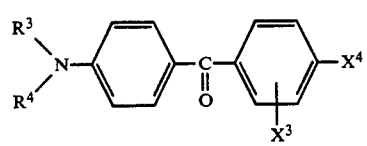
(VIII)

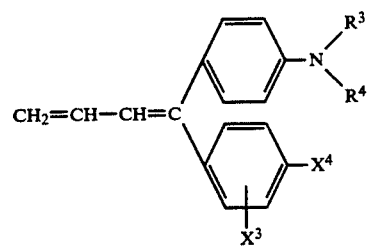
(IX)

Then, one mol of the butadiene derivative and one mol of a benzophenone derivative (compound of the following formula (X)) are condensated under the presence of a dehydrating agent such as anhydrous acetic acid, polyphosphoric acid or sulfuric acid to obtain a phthalide compound represented by the general formula (I) as substantially colorless crystals.

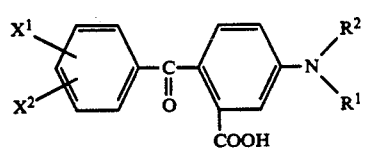
(X)

In the formulae (VIII), (IX) and (X), $R^1$, $R^2$ and $R^3$, $R^4$ and $X^1 \sim X^4$ have the same meaning as those in the formula (I).

As the butadiene compounds represented by the formula (IX), the following compounds can be exemplified.
1,1-bis(p-dimethylaminophenyl)-1,3-butadiene,
1,1-bis(p-diethylaminophenyl)-1,3-butadiene,
1,1-bis(p-dipropylaminophenyl)-1,3-butadiene,
1,1-bis(p-pyrrolidinophenyl)-1,3-butadiene,
1-(p-dimethylaminophenyl)-1-phenyl-1,3-butadiene,
1-(p-diethylaminophenyl)-1-phenyl-1,3-butadiene,
1-(p-dimethylaminophenyl)-1-(p-methoxyphenyl)-1,3-
   butadiene,
1-(p-dimethylaminophenyl)-1-(p-ethoxyphenyl)-1,3-
   butadiene,
1-(p-dimethylaminophenyl)-1-(p-propoxyphenyl)-1,3-
   butadiene,
1-(p-diethylaminophenyl)-1-(p-methoxyphenyl)-1,3-
   butadiene,
1-(p-dimethylaminophenyl)-1-(m,p-dimethoxyphenyl)-
   1,3-butadiene,
1-(p-dimethylaminophenyl)-1-(p-chlorophenyl)-1,3-
   butadiene,
1-(p-pyrrolidinophenyl)-1-(p-methoxyphenyl)-1,3-
   butadiene.

As the compound represented by the formula (X), the following compounds can be exemplified.
2-benzoyl-4-dimethylamino benzoic acid,
2-benzoyl-4-dipropylamino benzoic acid,
2-(4'-methoxybenzoyl)-4-dimethylamino benzoic acid,
2-(4'-methoxybenzoyl)-4-diethylamino benzoic acid,
2-(4'-methoxybenzoyl)-4-dipropylamino benzoic acid,
2-(4'-ethoxybenzoyl)-4-dimethylamino benzoic acid,
2-(4'-propoxybenzoyl)-4-dimethylamino benzoic acid,
2-(2',4'-dimethoxybenzoyl)-4-dimethylamino benzoic acid,
2-(2',4'-dimethoxybenzoyl)-4-diethylamino benzoic acid,
2-(2',4'-diethoxybenzoyl)-4-dimethylamino benzoic acid,
2-(2',4'-dimethoxybenzoyl)-4-dipropylamino benzoic acid,
2-(3',4'-dimethoxybenzoyl)-4-dimethylamino benzoic acid,
2-(3',4'-dimethoxybenzoyl)-4-diethylamino benzoic acid,
2-(3',4'-diethoxybenzoyl)-4-dimethylamino benzoic acid,
2-(3',4'-dimethoxybenzoyl)-4-dipropylamino benzoic acid,
2-(4'-chlorobenzoyl)-4-dimethylamino benzoic acid,
2-benzoyl-4-pyrrolidino benzoic acid,
2-benzoyl-4-piperidino benzoic acid,
2-(4'-methoxybenzoyl)-4-pyrrolidino benzoic acid,
2-(4'-methoxybenzoyl)-4-piperidino benzoic acid.

The compound represented by the formula (I) according to the present invention is used for producing pressure sensitive copying paper as the recording material by using known methods. For example, a coacervation method as described, for example, in U.S. Pat. Nos. 2,800,458 and 2,800,457 can be employed. Further, for producing heat sensitive recording paper as the recording material, a known method described, for example, in Japanese Patent Publication Sho 45-14039 (1970) may be adopted.

For producing the recording material such as the pressure sensitive copying paper and the heat sensitive recording paper, the compound according to the present invention can be used alone or as a mixture of two or more of them. By the mixing, the coloring property and the storage stability of image can be improved further. Further, for improving the hue of the color formed, coloring density and image stability more, known color couplers that form colors of various hues can be used together within a range not deteriorating the performance of the compound according to the present invention.

For instance, it can be used together with the color couplers having a following basic skeleton, for example, 3,3-bis(aminophenyl)-6-aminophthalide, 3,3-bis(indolyl)phthalide, 3-aminofluoran, aminobenzofluoran, 2,6-diaminofluoran, 2,6-diamino-3-methylfluoran, spiropyran, phenothiazine, phenoxazine, leucoauramine, diarylcarbazolylmethane, 3-indolyl-3-(aminophenyl)phthalide, 3-indolyl-3-(aminophenyl)azaphthalide, triaminofluorene phthalide and tetraaminodivinyl phthalide.

The pressure sensitive recording material (pressure sensitive copying paper) is produced, for example, as described below.

A phthalide compound represented by the formula (I) is dissolved in a solvent, dispersed together with a film-forming material in water and then formed into microcapsule by means of a coacervation method, an interface polymerization method, an in-situ method or the like. A binder is added to the microcapsule solution, which is coated and dried on a sheet or paper to form an upper paper sheet. Further, a developer is coated on a sheet of paper to form a lower paper sheet. They are overlaid to each other to obtain a pressure sensitive recording material. The ratio for the phthalide compound, the solvent and the film-forming material in the production of the microcapsules are in accordance with the known method.

As the solvent for dissolving the phthalide compound represented by the formula (I) as the color coupler, various kinds of solvents such as alkyl benzene, alkyl biphenyl, alkyl naphthalene, diallylethane, hydrogenated terphenyl or chlorinated paraffin series solvent can be used alone or in admixture. As the film-forming material, gelatin, gum arabic, polyester, polycarbonate, polyamide or polyurethane can be used.

As the binder for the microcapsules in the case of producing the pressure sensitive recording material, polyvinyl alcohol, methyl cellulose, hydroxyethyl cellulose, carboxymethyl cellulose, gum arabic, gelatin, casein, starch, polyvinyl pyrrolidone or styrene-maleic acid anhydride copolymer may be used.

As the developer, clays such as clay, bentonite, activated clay and acid clay, metal salts of salicylic acid derivatives, p-phenylphenol formalin resin, p-octylphenol formalin resin and their metal salts are used. Examples of the salicylic acid derivatives often used are as follows.

Salicylic acid, 3-methyl-5-tert-butyl salicylic acid, 3,5-di-tert-butyl salicylic acid, 3-cyclohexylsalicylic acid, 5-cyclohexylsalicylic acid, cresotinic acid, 5-nonylsalicylic acid, 5-cumylsalicylic acid, 3-phenylsalicylic acid, 2,5-dihydroxysalicylic acid, naphthoic acid, hydroxynaphthoic acid, 3-tertbutyl-5-α-methylbenzylsalicylic acid, 3,5-di(α-methylbenzyl)-salicylic acid. As polyvalent metals that form salts with such acids are zinc, magnesium, calcium, aluminum, nickel and copper. Among them, zinc, magnesium and calcium are preferred, zinc being particularly preferred.

In addition, it is also possible to use, for example, various antioxidants, UV-absorbers and surface active agents together as required.

Further, the heat sensitive recording material can be produced, for example, as follows. A phthalide compound represented by the formula (I) and a developer are separately pulverized each with a binder solution in a ball mill or the like, and zinc stearate or wax (for the improvement of the peelability from a thermal head) is added to a liquid dispersion obtained by mixing them for improving the performance of the heat sensitive recording material. The liquid dispersion is coated and dried on a support such as paper or film. The developer is used preferably by 50 to 400 parts by weight based on 100 parts by weight of the phthalide compound.

As the binder, polyvinyl alcohol, methyl cellulose, hydroxyethyl cellulose, carboxymethyl cellulose, gum arabic, gelatin, casein, starch, polyvinyl pyrrolidone or styrene-maleic anhydride copolymer may be used.

As the developer, hydroxy compounds such as
methyl p-hydroxybenzoate,
benzyl p-hydroxybenzoate,
2,2-bis(p-hydroxyphenyl)propane(bisphenol-A),
3,4'-isopropylidenediphenol,
2,2-bis(p-hydroxyphenyl)-4-methylpentane,
2,2-bis(4-hydroxy-3-allylphenyl)propane,
bis(4-hydroxyphenyl) acetic acid,
butyl 1,1-bis(4-hydroxyphenyl) acetate,
4,4'-cyclohexylidenephenol,
4,4'-thiodiphenol,
bis(4-hydroxy-3-methylphenyl)sulfide,
bis(4-hydroxy-3-tert-butyl-6-methylphenyl)sulfide,
4,4'-dihydroxydiphenylsulfone,
4-hydroxy-4'-methyldiphenylsulfone,
3,4-dihydroxy-4'-methyldiphenylsulfone,
4-hydroxy-4'-isopropoxydiphenylsulfone,
4,4'-dihydroxy-3,3'-dimethyldiphenylsulfone,
4,4'-dihydroxy-3,3'-diallyldiphenylsulfone, dimethyl 4-hydroxyphthalate,
bis(2-(4-hydroxyphenylthio)ethyl) ether,
4,4'-methylenebis(oxyethylenethio)diphenol,
1,1'-methylene-di-2-naphthol, and
p-hydroxyphenylsalicylamide can be used alone or in admixture.

Further, a sensitizing agent can be added if necessary.

As the sensitizing agent, paraffin wax, carnauba wax, higher fatty acid ester, higher fatty acid amide, dibenzyl oxalate, di-p-methylbenzyl oxalate, di-p-chlorobenzyl oxalate, phthalate, terephthalate, benzyl 4-benzyloxybenzoate, β-naphtholbenzyl ether, α-naphtholbenzyl ether, 1,4-dibenzyloxybenzene, 1,4-di(vinyloxyethoxy)-benzene, 1,2-diphenoxybenzene, 1,4-ditolyloxybenzene, 1,4-dialkoxynaphthalene, 1,5-dialkoxynaphthalene, m-terphenyl, p-benzylbiphenyl, dibenzylbenzene, 1,2-dixylylethane, 1-hydroxy-2-nathoate, 1,2-diphenoxyethane, 1,2-di(3-methylphenoxy)ethane, 1-(2-isopropylphenoxy)-2-naphthoxy(2)ethane, 1-phenoxyl-2-naphthoxy(1)ethane, bis(p-methoxyphenoxyethyl)-ether, 2-hydroxy-3-naphthoate, 4,4'-dialkoxydiphenylsulfone, benzamide, benzenesulfonamide, benzen sulfoneanilide, toluen sulfonanilide, phenyl toluene sulfonate and tolyl mesitylene sulfonate can be used alone or in admixture.

The phthalide compound represented by the formula (I) according to the present invention is a novel compound, which is almost colorless in itself and extremely stable in atmosphere, has no subliming property and discoloration of the background and is highly soluble to an organic solvent. Then, it rapidly forms a blue-blue black color by a developer and shows excellent light fastness and moisture proofness of color images. Further, since the color image has an intense absorption at 700~850 nm in addition to a visible region, it has a feature capable of being read by optical character reader (OCR, OMR) and bar code reader using near infrared rays.

Accordingly, it is a highly industrially valuable novel compound that can be used for usual recording material such as pressure sensitive copying paper and heat sensitive recording paper, as well as for a color coupler for infrared reading and recording material, for which a demand has been increased rapidly in recent years.

The present invention will now be described more specifically referring to examples but the invention is not restricted only to the following examples unless it does not go beyond the scope of the invention.

EXPERIMENTAL EXAMPLES

EXAMPLE 1

Synthesis of 3-(4-methoxyphenyl)-3-(1,1-bis(4-dimethylamino-phenyl)-1,3-butadienyl)-6-dimethylaminophthalide Into a glass reactor, 15.0 g of 2-(4'-methoxybenzoyl)-4-dimethylamino benzoic acid, 17.0 g of 1,1-bis(p-dimethylaminophenyl)-1,3-butadiene and 50 ml of anhydrous acetic acid were charged and stirred at 60° C. for 2 hours. Then, the reaction product was discharged into 500 ml of iced water and neutralized with sodium hydroxide. After filtering deposits, 200 ml of 10% sodium hydroxide and 200 ml of toluene were added to solids, which were stirred at 80° C. and then separated after confirming the complete dissolution. 10 g of activated clay and 10 g of activated carbon were added to the toluene layer and filtered after stirring at 80° C. for one hour. The filtrate was cooled and deposited crystals were filtered and dried to obtain 15.3 g of aimed crystals of light yellow color. m.p. 211°~214° C.

Yield: 53.4%.

It was confirmed by elemental analysis, IR absorption spectroscopy and NMR that it was the following compound.

IR (KBr, cm$^{-1}$) 3020, 2870, 2800, 1750, 1600, 1510, 1350, 1250, 1210

NMR (CDCl$_3$, ppm, 60 MHz) 3(18 H,S), 3.7(3 H,S), 5.9~7.5(18 H,m)

The compound rapidly formed blue color with activated clay and $\lambda_{max}$ in methanol-stannic chloride was 653 nm.

EXAMPLE 2

Synthesis of 3-(2,4-dimethoxyphenyl)-3-(1,1-bis(4-dimethylamino-phenyl)-1,3-butadienyl)-6-dimethylaminophthalide Into a glass reactor, 16.5 g of 2-(2',4'-dimethoxybenzoyl)-4-dimethylamino benzoic acid, 17.5 g of 1,1-bis(p-dimethylaminophenyl)-1,3-butadiene and 50 ml of anhydrous acetic acid were charged and stirred at 60° C. for 2 hours. Then, the reaction product was discharged into 500 ml of iced water and neutralized with sodium hydroxide. After filtration, 200 ml of 10% sodium hydroxide and 200 ml of toluene were added to solids, which were stirred at 80° C. and then separated after confirming the complete dissolution. Activated clay and activated carbon were added each by 10 g to the toluene layer and filtered after stirring at 80° C. for one hour. The toluene layer was cooled, and deposited crystals were filtered and dried to obtain 18.7 g of aimed crystals of light yellow color. m.p. 185°~187° C.

Yield: 62.0%.

It was confirmed by elemental analysis, IR absorption spectroscopy and NMR that it was the following compound.

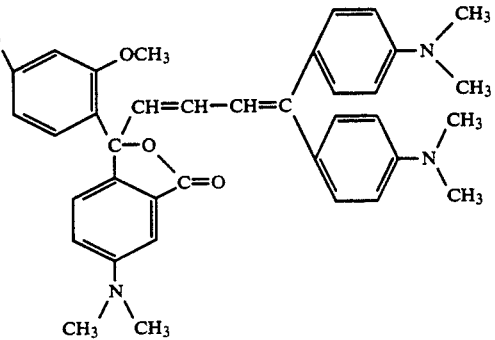

IR (KBr, cm$^{-1}$) 3020, 2870, 2790, 1750, 1600, 1510, 1350, 1250, 1220,

NMR (CDCl$_3$, ppm, 60 MHz) 3(18 H,S), 3.7(3 H,S), 3.8(3 H,S), 6.2~7.6(17 H,S)

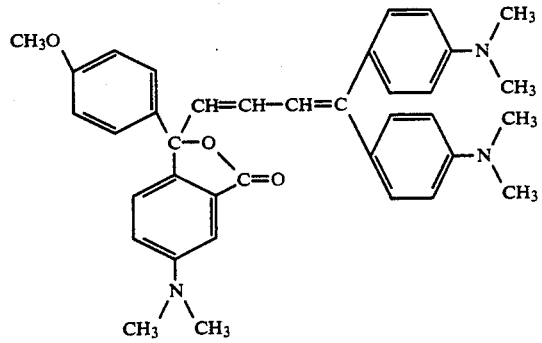

The compound rapidly formed blue color with activated clay and $\lambda_{max}$ in methanol-stannic chloride was 662 nm. 1,1-bis(p-dimethylaminophenyl)-1,3-butadiene used in these examples was synthesized as follows.

Into a glass reactor, 20 ml of ethylether, 8.2 g of magnesium and 0.05 g of iodine were charged, to which a solution of 20 g of allylbromide dissolved in 150 ml of ethylether was dropped for three hours and then reacted under reflux for three hours. After the reaction was over, 26.8 g of 4,4'-dimethylaminobenzophenone (Michler's ketone) was charged at a room temperature for two hours and then reacted for 2 hours. After the reaction was over, 40 ml of 10% hydrochloric acid was added gradually and, after distilling off the ether, 20 ml of toluene was added and separated after stirring at 80° C. for one hour. The toluene layer was cooled, and deposited crystals were filtered and dried to obtain 22.2 g of the aimed crystals. m.p. 105.5°~106.5° C.

Yield: 81.0%

EXAMPLES 3~17

Various butadiene derivatives and benzophenone derivatives were reacted in the same manner as in Example 1 or 2 to synthesize phthalide compounds shown in the following Table 1. Each of them was light yellow solid and rapidly formed blue color with activated clay.

ide solution was added and then further stirred at 50° C. for 30 min. After was adjusting pH to 4.5 by gradually adding a diluted acetic acid and stirring at 50° C. for about one hour, it was cooled to 0°~5° C. and further stirred for 30 min. Then, after adding 35 parts of an aqueous 4% glutar aldehyde solution gradually to harden capsules pH was adjusted to 6 with an aqueous diluted sodium hydroxide solution and then stirring was applied at a room temperature for several hours to complete capsulation. During the operation, coloring phenomenon did not occur at all.

The capsule solution was uniformly coated to a paper by a wire bar so that the weight after drying was 6 g/m$^2$ and then dried to obtain a capsule-coated paper (upper paper).

When the paper was laid over a paper coated with zinc 3,5-di($\alpha$-methylbenzyl)salicylate as a lower paper and manuscripted by a ball-point pen, dense blue characters rapidly appeared on the lower paper.

The color image was excellent in the light fastness and the moisture proofness and, since it had an intense absorption at 700~850 nm, it could be read by OCR. FIG. 1 shows the reflection spectra of the color image. Also, the capsule surface of the upper paper also showed excellent light fastness and there was no coloration or reduction in the coloration or coloring performance by the irradiation of sun light.

TABLE 1

| Example No. | R$^1$ | R$^2$ | R$^3$ | R$^4$ | X$^1$ | X$^2$ | X$^3$ | X$^4$ | Hue[1] | $\lambda_{max}$[2] (nm) |
|---|---|---|---|---|---|---|---|---|---|---|
| 3 | CH$_3$ | CH$_3$ | CH$_3$ | CH$_3$ | 4-CH$_3$O | H | H | CH$_3$O | Blue | 710 amorphous |
| 4 | CH$_3$ | CH$_3$ | CH$_3$ | CH$_3$ | 4-CH$_3$O | 3-CH$_3$O | H | N(CH$_3$)$_2$ | Blue | 653 mp 158~159° C. |
| 5 | C$_2$H$_5$ | C$_2$H$_5$ | CH$_3$ | CH$_3$ | 4-CH$_3$O | H | H | N(CH$_3$)$_2$ | Blue | 655 amorphous |
| 6 | n-C$_3$H$_7$ | n-C$_3$H$_7$ | CH$_3$ | CH$_3$ | 4-CH$_3$O | H | H | N(CH$_3$)$_2$ | Blue | 656 amorphous |
| 7 | CH$_3$ | CH$_3$ | CH$_3$ | CH$_3$ | 4-C$_2$H$_5$O | H | H | N(CH$_3$)$_2$ | Blue | 654 |
| 8 | CH$_3$ | CH$_3$ | C$_2$H$_5$ | C$_2$H$_5$ | 4-CH$_3$O | H | H | N(C$_2$H$_5$)$_2$ | Blue | 658 amorphous |
| 9 | CH$_3$ | CH$_3$ | C$_2$H$_5$ | C$_2$H$_5$ | 4-CH$_3$O | 3-CH$_3$O | H | N(C$_2$H$_5$)$_2$ | Blue | 675 |
| 10 | CH$_3$ | CH$_3$ | CH$_3$ | CH$_3$ | 4-CH$_3$O | H | H | C$_2$H$_5$O | Blue | 712 |
| 11 | CH$_3$ | CH$_3$ | CH$_3$ | CH$_3$ | 4-C$_2$H$_5$O | 2-C$_2$H$_5$O | H | N(CH$_3$)$_2$ | Blue | 665 |
| 12 | CH$_3$ | CH$_3$ | CH$_3$ | CH$_3$ | 4-Cl | H | H | N(CH$_3$)$_2$ | Blue | 670 |
| 13 | CH$_3$ | CH$_3$ | CH$_3$ | CH$_3$ | H | H | H | N(CH$_3$)$_2$ | Blue | 655 |
| 14 | CH$_3$ | CH$_3$ | CH$_3$ | CH$_3$ | 4-CH$_3$O | H | H | Cl | Blue | 715 |
| 15 | CH$_3$ | CH$_3$ | CH$_3$ | CH$_3$ | 4-CH$_3$O | H | 3-CH$_3$O | CH$_3$O | Blue | 710 mp 185~188° C. |
| 16 | —CH$_2$—CH$_2$—CH$_2$—CH$_2$— | | CH$_3$ | CH$_3$ | 4-CH$_3$O | H | H | N(CH$_3$)$_2$ | Blue | 648 |
| 17 | CH$_3$ | CH$_3$ | —CH$_2$—CH$_2$—CH$_2$—CH$_2$— | | 4-CH$_3$O | H | H | 1-Pyrrolidinyl | Blue | 650 |

[1] on activated clay
[2] in methanol-stannic chloride

EXAMPLE 18

Preparation Example for Pressure Sensitive Copying Paper

Five parts (by weight, here and hereinafter) of 3-(2,4-dimethoxyphenyl)-3-(1,1-bis(4-dimethylaminophenyl)-1,3-butadienyl)-6-dimethylaminophthalide obtained in Example 2 was dissolved in 95 parts of monoisopropyldiphenyl, to which a solution containing 24 parts of gelatin and 24 parts of gum arabic dissolved in 400 parts of water and adjusted to pH 7 was added and emulsified by using a homogenizer. After adding 100 parts of warm water to the emulsion and stirring at 50° C. for 30 min, about one part of an aqueous 10% sodium hydrox-

COMPARATIVE EXAMPLE 1

A pressure sensitive copying paper was obtained by the same procedures as in Example 18 except for using 5 parts of the compound of the formula (II) as the color coupler. The pressure sensitive copy paper formed clear blue color but had no absorption in the near infrared region and, accordingly, could not be read by OCR. The reflection spectra of the color image are shown in FIG. 1. In FIG. 1, the reflection spectra of images are shown at 1 for Example 18 and at 2 for Comparative Example.

EXAMPLE 19

Preparation Example of Heat Sensitive Recording Paper (1) Preparation of Color Coupler Dispersion (A)

| | |
|---|---|
| 3-(4-methoxyphenyl-3-(1,1-bis(4-dimethylaminophenyl)-1,3-butadienyl)-6-dimethylaminophthalide (Example 1) | 5 parts |
| Kaolinite | 15 parts |
| Aqueous 10% solution of polyvinyl alcohol | 100 parts |
| Water | 85 parts |

The mixture described above was pulverized by a paint shaker (manufactured by Toyo Seiki K. K.) till the average grain size of the color coupler was reduced to 1 μm.

(2) Preparation of Developer Dispersion (B)

| | |
|---|---|
| Bisphenol A | 15 parts |
| Zinc stearate | 10 parts |
| Aqueous 10% polyvinyl alcohol solution | 150 parts |

The mixture described above was pulverized by a paint shaker till the average grain size was reduced to 2 μm.

(3) Preparation and Coating of Heat Sensitive Coating Solution

A heat sensitive coating solution was obtained by mixing and stirring 10 parts of the dispersion (A) and 6.5 parts of the dispersion (B). The coating solution was uniformly coated by a wire bar on a sheet of paper so that the weight after drying was 6 g/m² and then dried to obtain heat sensitive recording paper.

Figure 2:
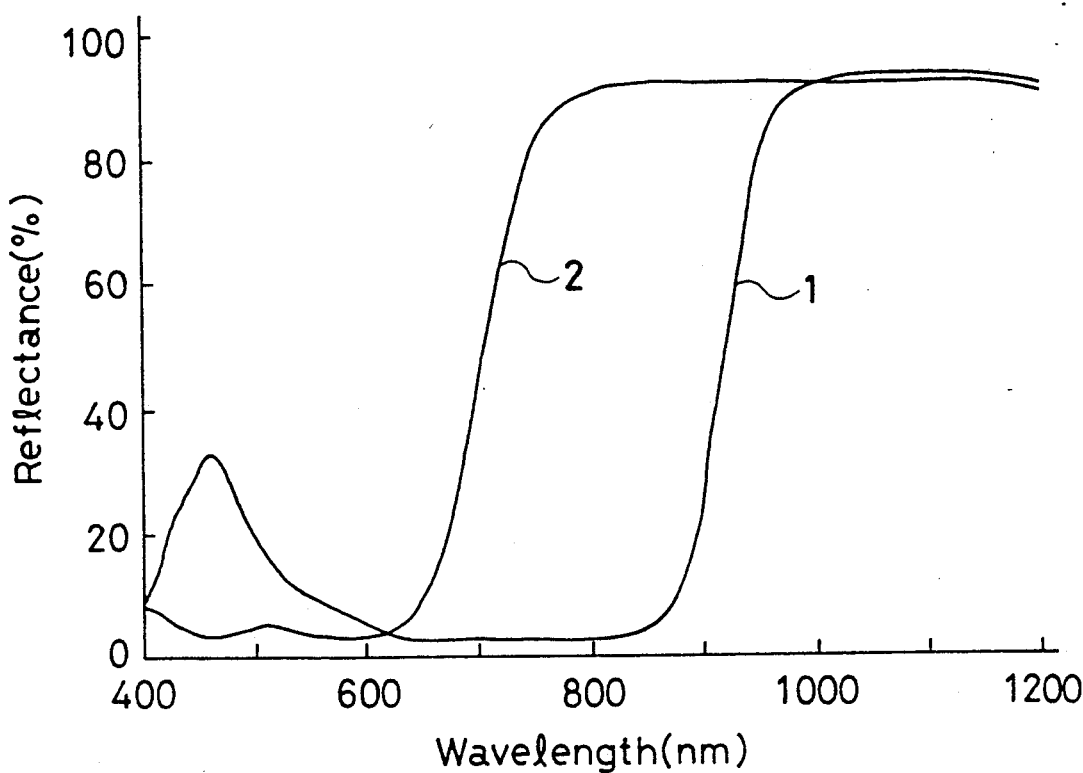
FIG. 2 shows reflection spectra of images in Example 2 and Comparative Example 2.
Figure 3:
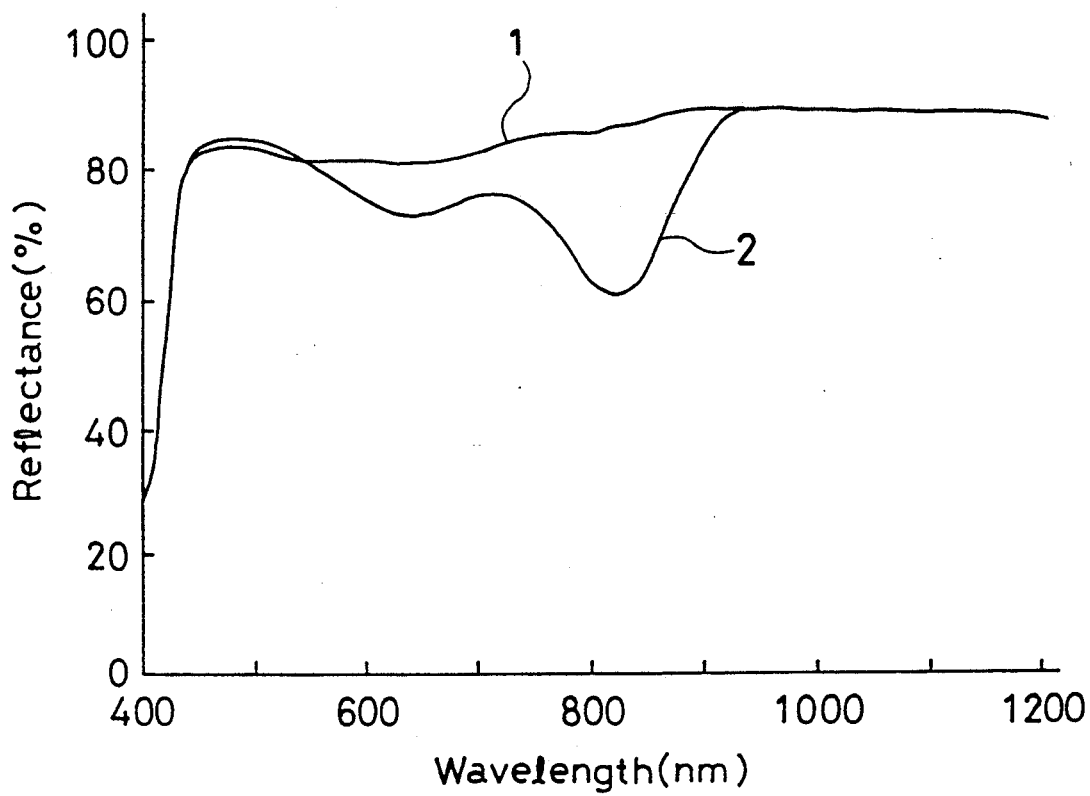
FIG. 3 shows reflection spectra of background in Example 2 and Comparative Example 2.

The heat sensitive recording paper was almost colorless with no discoloration of the background and formed dense blue-black color rapidly by heating with a thermal pen or the like. The color image formed was excellent in the light fastness and the moisture proofness and since it had an intense absorption at 700~850 nm, it could be read by OCR. FIG. 2 shows the reflection spectra of the color image and FIG. 3 shows the reflection spectra of the background portion.

Further, the coated surface was also excellent in the light fastness and no coloration due to sunlight irradiation occurred.

COMPARATIVE EXAMPLE 2

A heat sensitive recording paper was obtained by the same procedures as those in Example 19 excepting for using 5 parts of the compound represented by the formula III as a color coupler. The heat sensitive recording paper formed black color under heating by a thermal pen or the like but, since it had no absorption at all in the near infrared region, it could not be read out by OCR. The reflection spectra of the color image are shown in FIG. 2. In FIG. 2, reflection spectra are shown at 1 for Example 19 and at 2 for Comparative Example 2.

COMPARATIVE EXAMPLE 3

A sheet of heat sensitive recording paper was obtained by the same procedures as those in Example 19 except for using 5 parts of the compound represented by the formula V as a color coupler. The heat sensitive recording paper formed blue-green color under heating by a thermal pen or the like and had absorption in the near infrared region but showed yellow-green discoloration of the background. Accordingly, contrast between the background and the color image area was reduced. FIG. 3 shows the reflection spectra for the background portion. In FIG. 3, reflection spectra are shown at 1 for Example 19 and at 2 for Comparative Example.

COMPARATIVE EXAMPLE 4

A sheet of heat sensitive recording paper was obtained in the same procedures as those in Example 19 except for using 5 parts of 3-(4-diethylaminophenyl)-3-(1,1-bis(4-dimethylaminophenyl)-1,3-butadienyl)phthalide as a color coupler. When the heat sensitive recording paper was heated by a thermal pen or the like, it formed blue-green color and showed absorption also in the near infrared region, but it caused yellow-green discoloration of the background.

It has been confirmed from Examples and Comparative Examples that the recording material according to the present invention is excellent.

What is claimed is:

1. A phthalide compound represented by the formula (I):

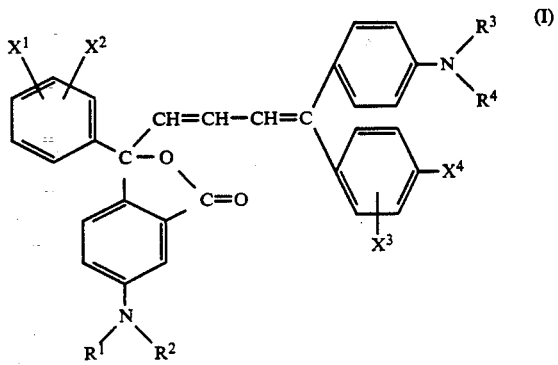

where $R^1$ and $R^2$ represent, independently, alkyl group having 6 or less carbon atoms; cycloalkyl group having 5 or 6 carbon atoms; aryl group; or $R^1$, $R^2$ and N can be taken together to form a pyrrolidino group or a piperidine group, $R^3$ and $R^4$ represent, independently, alkyl group having 6 or less carbon atoms; cycloalkyl group having 5 or 6 carbon atoms; aryl group; or $R^3$, $R^4$ and N can be taken together to form a pyrrolidino group or a piperidine group, $X^1 \sim X^3$ represent, independently, hydrogen atom, alkyl group having 6 or less carbon atoms, alkoxy group having 6 or less carbon atom or halogen atom, and $X^4$ represents hydrogen atom, alkyl group having 6 or less carbon atoms, alkoxy group having 6 or less carbon atom, halogen atom or

2. A recording material containing the phthalide compound according to claim 1 as a color coupler.

3. The recording material according to claim 2, wherein the recording material is a pressure sensitive recording material or a heat sensitive recording material.